United States Patent [19]

Chang

[11] Patent Number: 5,368,575
[45] Date of Patent: Nov. 29, 1994

[54] URETHRAL CATHETER HOLDER

[76] Inventor: Hau H. Chang, 7704 Calle Espada, Bakersfield, Calif. 93309

[21] Appl. No.: 162,229

[22] Filed: Dec. 6, 1993

Related U.S. Application Data

[63] Continuation-in-part of Ser. No. 964,301, Oct. 21, 1992, abandoned.

[51] Int. Cl.$^5$ ............................................. A61M 5/32
[52] U.S. Cl. ..................... 604/174; 128/912; 128/DIG. 26; 604/263; 604/349; 604/351; 604/171; 604/175; 604/280
[58] Field of Search ............... 128/DIG. 26, DIG. 25, 128/918, 917, 912; 604/167, 171, 172, 174, 175, 176, 177, 179, 180, 263, 265, 280, 344–347, 349, 351, 352, 353, 354, 355, 322, 326, 327, 332

[56] References Cited

U.S. PATENT DOCUMENTS

| | | | |
|---|---|---|---|
| 4,397,647 | 8/1983 | Gordon | 604/180 |
| 4,498,903 | 2/1985 | Mathew | 604/179 |
| 4,699,616 | 10/1987 | Nowak et al. | 604/180 |
| 4,710,169 | 12/1987 | Christopher | 604/265 |
| 4,897,082 | 1/1990 | Erskine | 604/177 |
| 5,069,206 | 12/1991 | Crosbie | 604/174 |
| 5,226,892 | 7/1993 | Boswell | 604/180 |

Primary Examiner—C. Fred Rosenbaum
Assistant Examiner—Ronald K. Stright, Jr.

[57] ABSTRACT

An Urethral Catheter Holder is a device that has two semicylindric elements hinged with each other by a flexible living hinge on one edge. It has a single non adjustable male and female locking tooth on the other edges opposite to the living hinge. It has a semicylindric rim extension at one end of the device that extends to a diameter larger than said semicylindrical segment. There is a wedge defect at the living hinge side of the rim extension. The defect of the rim extension is covered by the curve extension cover. There is a compressible foam pad lining the surface of the semicylindric element and rim extension. The foam pad on the rim extension is impregnated with antimicrobial agent. When the device is placed in operative position, it forms a lumen inner to the foam pads able to hold and affix the Foley catheter without compromising and distorting the lumen of the catheter and the balloon inflation and deflation tube. It also provides a semi closed housing space for the male external urethral meatus and allows contact between the antimicrobial ointment and said urethral meatus. It reduces the incidence of ascending cather associated urinary tract infection.

8 Claims, 3 Drawing Sheets

URETHRAL CATHETER HOLDER

This is a continuation-in-part of my prior application Ser. No. 07/964,301 filed on Oct. 21, 1992 now abandoned.

BACKGROUND OF THE INVENTION

1. Field Of The Invention

The invention relates to a device that can be clipped on the urethral Foley catheter immediately external to the male urethral meatus after the Foley catheter is inserted soon after the transurethral resection of the prostate. This is done to keep the inflated balloon within the prostatic fossa to achieve the hemostasis during the post operative period. It also provides a housing space to keep the antimicrobial ointment constantly at the male external urethral meatus in anyone who wears an indwelling Foley catheter in order to reduce nosocomial and community acquired urinary tract infection.

2. Description Of The Prior Art

In a conventional surgery of the prostate such as "The Transurethral Resection Of The Prostate", a concave cavity is created in the prostatic urethra. Venous sinus bleeding usually is controlled by inflating the Foley catheter balloon in the prostatic fossa. It happens that the balloon of the Foley catheter frequently is dislodged and slips into the bladder. Profuse bleeding from the prostatic fossa therefore occurs. In the conventional practice, the bleeding is usually controlled by applying a traction to the Foley catheter balloon and tapeing the Foley catheter on the patients thigh.

The antiseptic ointments such as Neosporin (Neomycin sulfate-polymyxin B sulfate) or Betadine (providone-Iodine) ointment are routinely applied to the external urethral meatus to lubricate the urethral mucosa and to prevent ascending urinary tract infection in anyone who wears the indwelling Foley catheter in the present medical practice, however the ointment will soon be removed by the covering linen or patients underwear. It becomes air dry causing discomfort to the patient. Ascending urinary tract infection through contamination to the external urethral meatus soon follows.

There has been no specific device that can be mounted on the indwelling Foley catheter that provides the following functions simultaneously: 1) To be able to affix the balloon of the Foley catheter within the prostatic fossa. 2) To be able to keep the antiseptic ointment at the external urethral meatus constantly without external contact and air exposure. 3) To be able to provide a smooth grip to the different sizes of Foley catheters without distorting the lumen of the Foley catheter and obstructing the balloon inflation and deflation tube.

SUMMARY OF THE INVENTION

The Urethral Catheter Holder is a short segment of tubular structure. It has a concave extension on one end. It consists of a pair of semicylindric elements. One edge of each element is hinged together by a living hinge or web. The other edges can have non adjustable male and female locking teeth. The inner surface in the entire device, including the extension rim, is covered by a layer of compressable foam pad. The foam pad lining of the extension rim is impregnated with antimicrobial agent such as Neosporin (Neomycin sulfate-polymyxin B sulfate) or Betadine (providone-Iodine). When these two semicylindric elements are snapped together, it forms a constant diameter tubular space in the center to accommodate the urethral Foley catheter. It also forms a stadium shaped space at one end to accommodate the glans penis and the urethral meatus.

The compressable foam pad in a constant diameter lumen and in a non or little adjustable locking cylindric element enables it to produce a smooth gentle grip to different sizes of Foley catheter without compromising or distorting the lumen of the Foley catheter and the tube along side of the Foley catheter leading to the balloon.

The objective of the present invention is to resolve some of the problems and difficulties in current medical and urological practices. In a surgical procedure called "Transurethral Resection Of The Prostate" or "Suprapubic Prostatectomy", a Foley catheter balloon is usually inflated in the prostatic fossa to stop the venous sinus bleeding. The balloon is usually displaced into the bladder as soon as the patient amubulates during the postoperative period. Profuse bleeding usually occurs. In a situation when a patient needs a short term or a long term indwelling Foley catheterization, either in the perioperative period or in the state of urinary retention or in neurogenic bladder dysfuction, a Foley catheter is usually left indwelling for several days or weeks. Air exposure and direct external contact of the urethral meatus by the linen and patients underwear frequently causes discomfort and ascending urinary tract infection through the external urethral meatus.

The present invention is a multifunctional device. It possesses all of the problem solving features in one device. Unlike other medical tube fixation and fitment devices, it has the following unique features: 1) There is a simple single non-adjustable locking tooth. It is easy to engage and disengage. It produces a round constant symmetrical tubular space in the center of the device to accommodate the urethral Foley catheter without distorting disconfigurating or narrowing the lumen of the Foley catheter and the balloon tube. It allows the irrigation fluid, debrides, sediments and small blood clots to flow freely. It also allows the water in the balloon to flow in and out freely. Other prior inventions with adjustable locking device for medical tube fitment tends to produce unequal space proximal and distal to the locking device, therefore distorting the medical tubes. 2) It has a constant diameter inner lumen as described above. 3) It produces a uniform smooth grip to the Foley catheter. 4) It does not obstruct the balloon ingress and egress tube. 5) The presence of the compressable foam pad in the lumen of the device will adjust itself to accommodate different sizes of the Foley catheter. 6) It has a stadium shaped space to accommodate the glans penis and the antimicrobial ointment. It prevents external and air contact to male urethral meatus. It provides comfort to the patient. It reduces the chance of ascending urinary tract infection. 7) It provides traction to the Foley catheter to maintain the position of the balloon within the prostatic fossa.

BRIEF DESCRIPTION OF THE DRAWING

The Urethral Catheter Holder in accordance with the present invention will now be described by way of example with reference to the accompanying drawing.

DESCRIPTION OF THE PREFERRED EMBODIMENT

Figure 1:
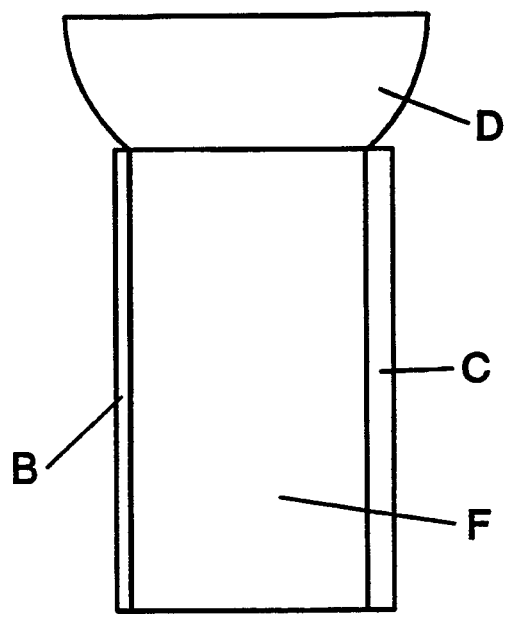
FIG. 1 is an external side view of The Urethral Catheter Holder.
Figure 2:
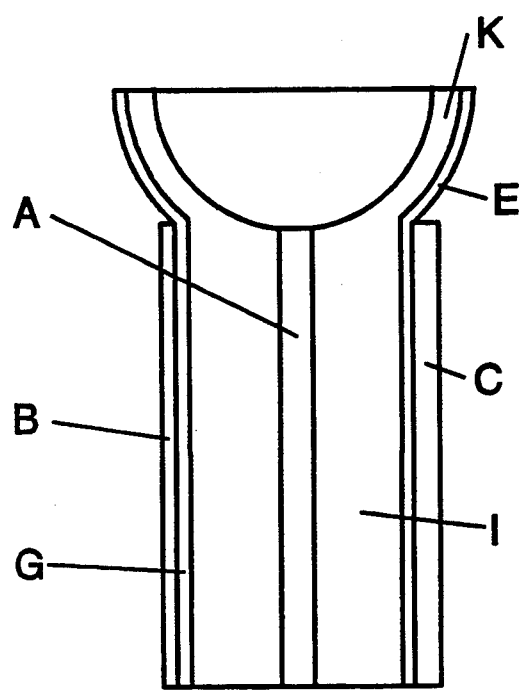
FIG. 2 is a longitudinal section view of the Urethral Catheter Holder.
Figure 3:
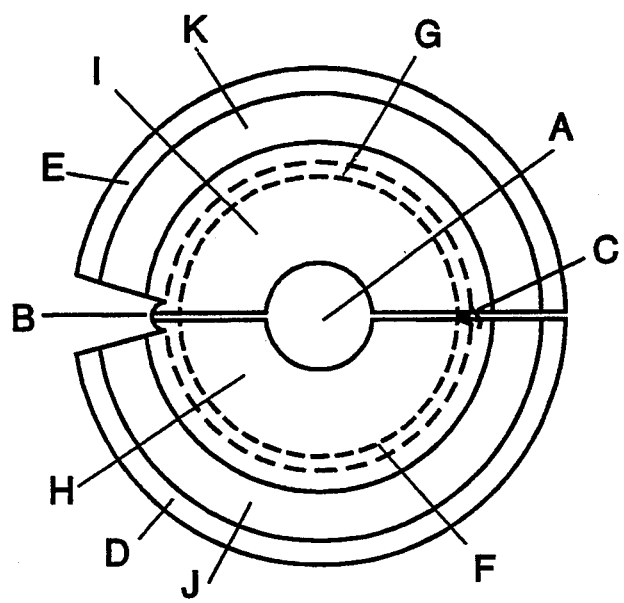
FIG. 3 is a external top view of the Urethral Catheter Holder.
Figure 4:
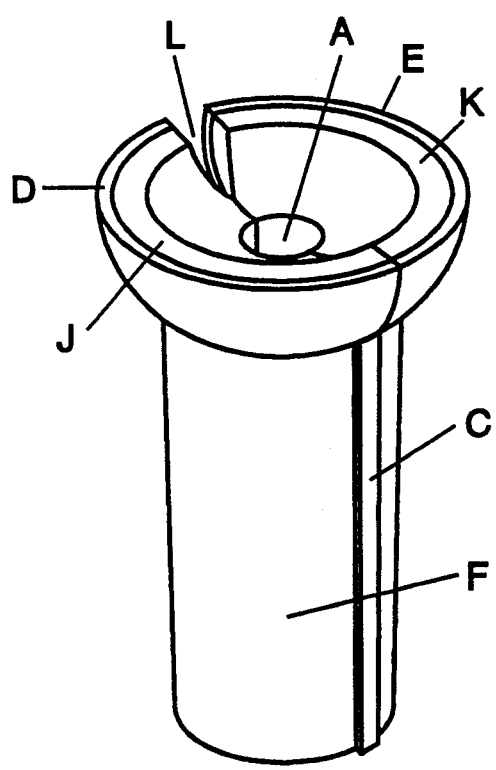
FIG. 4 is a three dimentional external view of the Uretheral Catheter Holder.
Figure 5:
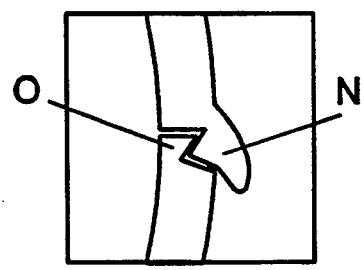
FIG. 5 is the magnification view of the locking mechanism of the device.
Figure 6:
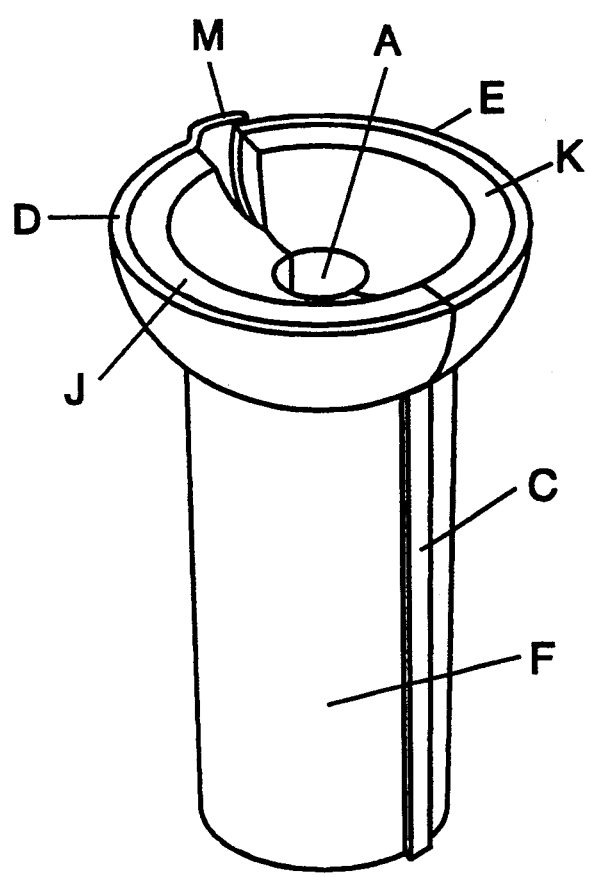
FIG. 6 is a three dimentional external view of the urethral catheter holder showing rim extension covering the wedge defect.

Referring to the FIG. 1, 2, 3 an embodiment of the Urethral Foley Catheter Holder in side views and top views are illustrated. The device is consisted of two parts, Part F & G. Each of these is a half of a segment of a tubular structure, when assembled they form a cylindric tube with a lumen in the center. Within the lumen there is a foam pad, H & I, there is a concave shaped rim extension D & E at one end of the Catheter Holder. The inner surface of the rim extension is also padded with a foam pad, J & K. A tubular space A in the center of the foam pad is created to accommodate the Foley Catheter. The semi-tubular elements F & G are hinged together at one side edges, B,s by a living hinge or a web. The other side edges, C,s, can be snapped together as shown in FIG. 3, 4, 5 & 6. FIG. 5 is a magnification of cross section view of the locking mechanism at Edges, C,s. N is the male locking mechanism, 0 is the female locking mechanism. Foam pad on the rim extension J & K is impregnated with antimicrobial agent (such as Neomycin sulfate-polymyxin B sulfate and porodine-Iodine). There is a wedge defect on D & E at B edge to allow the F & G elements to open at C edge for inserting the Foley catheter into lumen A. In order to keep antibiotics ointment and glans penis more in close space within the stadium shape rim extension, a curve extension M of rim D is made to cover the wedge defect L, as shown in FIG. 6. The glans penis should be pulled back during the application or removal of the catheter holder to avoid the injury.

Although detailed embodiments of the invention are illustrated in the drawings and previously described in detailed, this invention contemplates any configuration, dimension, design and relationships of components which will function in a similar manner and which will provide the equivalent result.

I claim:

1. A urethral Foley catheter holder for gripping an indwelling urethral Foley catheter and impregnating an antimicrobial agent at the urethral meatus comprising:
   a) a first short semicylindrical segment with a semicylindrical rim extension at one end that extends to a diameter larger than said short semicylindrical segment, said short segment comprising a foam pad lining the inner surface thereof and said rim extension comprising a foam pad impregnated with an antimicrobial agent lining the inner surface thereof;
   b) a second short semicylindrical segment with a semicylindrical rim extension at one end that extends to a diameter larger than said short semicylindrical segment, said short segment comprising a foam pad lining the inner surface thereof and said rim extension comprising a foam pad impregnated with an antimicrobial agent lining the inner surface thereof;
   c) a living hinge or web at one edge of each short semicylindrical segment to allow connection of said short semicylindrical segments together to form a tubular structure with a central lumen inner of the foam pads to accommodate the Foley catheter; and
   d) a locking mechanism comprising a male locking tooth on said first short semicylindrical segment on the edge opposite said hinge or web and a female locking notch on said second short semicylindrical segment on the edge opposite said hinge or web to facilitate locking the device in an operative position.

2. The urethral catheter holder according to claim 1 further comprising a wedge defect on each said semicylindrical rim extension at the hinged or webbed edge, to facilitate the opening of the device and accommodation of the Foley catheter in the central lumen.

3. The urethral catheter holder according to claim 2, wherein one wedge defect has a curve extension cover thereon.

4. The urethral catheter holder according to claim 1, wherein the male locking tooth is nonadjustable.

5. The urethral catheter holder according to claim 1, wherein the foam pads produce a constant tubular space to accommodate the urethral Foley catheter.

6. The urethral catheter holder according to claim 1, wherein the lumen is able to accommodate the Foley catheter and a balloon inflation and deflation tube and wherein the device produces a firm smooth grip on the urethral Foley catheter without distorting, compromising or obstructing the lumen of the catheter or said inflation and deflation tube.

7. The urethral catheter holder according to claim 1, wherein the rim extensions produce a semi-closed housing space for the male external urethral meatus and allows contact between the antimicrobial ointment and said urethral meatus.

8. The urethral catheter holder according to claim 1, wherein the device is a multifunctioning device suitable for fixing an indwelling urethral Foley catheter and for reducing the incidence of nosocomial and community acquired ascending urinary tract infection.

* * * * *